United States Patent [19]

Goldberg et al.

[11] Patent Number: 4,758,512
[45] Date of Patent: Jul. 19, 1988

[54] HOSTS AND METHODS FOR PRODUCING RECOMBINANT PRODUCTS IN HIGH YIELDS

[75] Inventors: Alfred L. Goldberg, Brookline; Stephen A. Goff, Boston; Lawrence P. Casson, Sommerville, all of Mass.

[73] Assignee: President and Fellows of Harvard College, Cambridge, Mass.

[21] Appl. No.: 586,786

[22] Filed: Mar. 6, 1984

[51] Int. Cl.$^4$ .................... C12P 21/00; C12N 15/00;

[52] U.S. Cl. ................................ 435/68; 435/172.1; 435/172.3; 435/839; 435/849; 935/16; 935/72; 935/73; 935/74

[58] Field of Search .................. 435/68, 70, 71, 172.1, 435/172.3, 317, 253, 839, 849, 240; 935/1–14, 22, 111, 73, 74; 260/112 R

[56] References Cited

FOREIGN PATENT DOCUMENTS

| 55945 | 7/1982 | European Pat. Off. . |
| 0072925 | 2/1983 | European Pat. Off. . |
| WO83/00702 | 3/1983 | PCT Int'l Appl. . |
| WO85/0394-99 | 9/1985 | PCT Int'l Appl. . |
| 2119804B | 11/1983 | United Kingdom . |

OTHER PUBLICATIONS

Neidhardt, Van Bogelen and Lau, J. Bacteriol., 153: 597–603, 1983 (Feb.).
Neidhardt and Van Bogelen, Biochem. and Biophys. Res. Comm., 100: 894–900, 1981.
Bachmann, Microbiol. Rev., 47: 180–230, 1983 (Jun.).
T. A. Baker et al., "Proteolysis Defect in htpR Mutants of *E. Coli*", Abstracts of papers presented at *Phage and Bacterial Regulatory Mechanisms*, Cold Spring Harbor, New York, p. 87 (Aug. 23–28, 1983).
V. G. Corces et al., "Localization of Sequences Responsible for Heat Shock Induced Transcription", *J. Cell. Biochem. Suppl.*, O(6), p. 340 (1982).
C. H. Chung et al., "The Product of the lon (capR) Gene in *Escherichia coli* is the ATP-Dependent Protease, Protease La", *Proc. Natl. Acad. Sci. USA*, 78 (No. 8), pp. 4931–4935 (Aug. 1981).
C. H. Chung et al., "Studies of the Protein Encoded by the lon Mutation, CapR9, in *Echerichia coli*", *J. Biol. Chem.*, 258 (No. 1), pp. 215–221 (Jan. 10, 1983).
K. E. Davies, "A Comprehensive List of Cloned Eukaryotic Genes", *Genetic Engineering*, 3, Williamson (ed.), Academic Press, New York, pp. 143–173 (1982).
M. Desautels et al., "Demonstration of an ATP-Dependent, Vanadate-Sensitive Endoprotease in the Matrix of Rat Liver Mitochondria", *J. Biol. Chem.*, 257 (No. 19), pp. 11673–11679 (Oct. 10, 1982).
S. Gottesman et al., "Deg Phenotype of *Escherichia coli* lon Mutants", *J. Bacteriol.*, 133 (No. 2), pp. 844–851 (Feb. 1978).
A. D. Grossman et al., "Mutations in the lon Gene of *E. coli* K12 Phenotypically Suppress a Mutation in the Sigma Subunit of RNA Polymerase", *Cell*, 32, pp. 151–159 (Jan. 1983).
M. Houghton et al., "The Complete Amino Acid Sequence of Human Fibroblast Interferon as Deduced Using Synthetic Oligodeoxyribonucleotide Primers of Reverse Transcriptase", *Nucleic Acids Res.*, 8 (No. 13), pp. 2885–2894 (1980).

(List continued on next page.)

Primary Examiner—Thomas G. Wiseman
Assistant Examiner—Thomas D. Mays
Attorney, Agent, or Firm—James F. Haley, Jr.; Teresa L. Solomon

[57] ABSTRACT

This invention relates to improved host organisms and methods for producing recombinant products in high yields. More particularly, the present invention relates to cell strains carrying specific mutations within their DNA sequences which cause the organism to exhibit a reduced capacity for degrading foreign products and the use of these strains to produce increased yields of genetically engineered foreign proteins, polypeptides and other products. The methods disclosed in this invention advantageously permit the production, in high yields, of foreign recombinant proteins, polypeptides or other products in hosts which do not usually produce such products.

7 Claims, 3 Drawing Sheets

DEGRADATION OF PUROMYCYL FRAGMENTS IN E. COLI

OTHER PUBLICATIONS

D. G. Klapper et al., "Sequence Analysis of Somatomedin-C: Confirmation of Identity with Insulin-Like Growth Factor I", *Chemical Abstracts*, 99, Abstract No. 48021d (1983), of *Endocrinology*, 112, pp. 2215-2217 (1983).

J. D. Kowit et al., "Intermediate Steps in the Degradation of a Specific Abnormal Protein in *Escherichia coli*", *J. Biol. Chem.*, 252 (No. 23), pp. 8350-8357 (Dec. 10, 1977).

F. S. Larimore et al., "Studies of the ATP-Dependent Proteolytic Enzyme, Protease La, From *Escherichia coli*", *J. Biol. Chem.*, 257 (No. 8), pp. 4187-4195 (Apr. 25, 1982).

S. Lin et al., "β-Galactosidase: Rates of Synthesis and Degradation of Incomplete Chains", *J. Biol. Chem.*, 247 (No. 7), pp. 2205-2211 (Apr. 10, 1972).

F. C. Neidhardt et al., "The High-Temperature Regulon of *Escherichia coli*", in *Heat Shock: From Bacteria to Man*, M. J. Schlesinger et al. (ed.), Cold Spring Harbor Laboratory, Cold Spring Harbor, New York, pp. 139-145 (1982).

K. Olden et al., "Studies of the Energy Requirement for Intracellular Protein Degradation in *Escherichia coli*", *Biochim. et Biophys. Acta*, 542, pp. 385-398 (1978).

T. M. Roberts et al., "A General Method for Maximizing the Expression of a Cloned Gene", *Proc. Natl. Acad. Sci. USA*, 76 (No. 2), pp. 760-764 (Feb. 1979).

W. J. Rutter, "Production of 'Valuable' Proteins in Alternate Biological Hosts", in *Recombinant DNA and Genetic Experimentation*, J. Morgan et al., (eds.), Pergamon Press, pp. 123-128 (1979).

B. Shineberg et al., "The lon Gene and Degradation of β-Galactosidase Nonsense Fragments", *J. Bacteriol.*, 116 (No. 3), pp. 1469-1471 (Dec. 1973).

A. St. John et al., "Further Evidence for the Involvement of Charged tRNA and Guanosine Tetraphosphate in the Control of Protein Degradation in *Escherichia coli*", *J. Biol. Chem.*, 253 (No. 11), pp. 3945-3951 (Jun. 10, 1978).

K. H. S. Swamy et al., "*E. Coli* Contains Eight Soluble Proteolytic Activities, One Being ATP Dependent", *Nature*, 292 (No. 5824), pp. 652-654 (Aug. 13, 1981).

K. Tilly et al., "Identification of the Heat-Inducible Protein C15.4 as the groES Gene Product in *Escherichia-coli*", *J. Bacteriol.*, 154 (No. 3), pp. 1505-1507 (Jun. 1983).

K. Tilly et al., "The dnaK Protein Modulates the Heat-Shock Response of *Escherichia coli*", *Cell*, 34, pp. 641-646 (Sep. 1983).

T. Tobe et al., "Isolation and Physical Mapping of Temperature-Sensitive Mutants Defective in Heat-Shock Induction of Proteins in *Escherichia coli*", *Mol. Gen. Genet.*, 195, pp. 10-16 (1984).

L. Waxman et al., "Protease La from *Escherichia coli* Hydrolyzes ATP and Proteins in a Linked Fashion", *Proc. Natl. Acad. Sci. USA*, 79, pp. 4833-4887 (Aug. 1982).

T. Yamamori et al., "Temperature-Induced Synthesis of Specific Proteins in *Escherichia coli*: Evidence for Transcriptional Control", *J. Bacteriol.*, 142 (No. 3), pp. 843-851 (Jun. 1980).

T. Yamamori et al., "*Escherichia coli* Gene (hin) Controls Transcription of Heat-Shock Operons and Cell Growth at High Temperature", in *Heat Shock: From Bacteria to Man*, M. J. Schlesinger et al. (ed), Cold Spring Harbor Laboratory, Cold Spring Harbor, New York, pp. 131-137 (1982).

D. N. Arnosti et al., "Characterization of Heat Shock in Bacillus Subtilis", *J. Bacteriol.*, 168 (No. 3) pp. 1243-1249, (Dec. 1986).

G. Buell et al., "Optimizing the Expression in *E. coli* of a Synthetic Gene Encoding Somatomedin-C (IGF-I)", *Nucleic Acids Res.*, 13 (No. 6), pp. 1923-1938 (1985).

A. J. Carr et al., "Escherichia coli Mutants Defective in the Degradation of Abnormal Proteins", *Biochem. Society Transactions*, p. 337, 610th Meeting, Stirling (Sep. 1985).

D. Downs et al., "Isolation and Characterization of Ion Mutants in *Salmonella typhimurium*", *J. Bacteriol.*, 165 (No. 1), pp. 193-197 (Jan. 1986).

A. L. Goldberg and S. A. Goff, "The Selective Degradation of Abnormal Proteins in Bacteria", *Maximizing Gene Expression*, W. Reznikoff and L. Gold (eds.) Chapter 9, pp. 287-314 (Butterworths 1986).

M. R. Maurizi et al., "Insertional Mutagenesis of the Ion Gene in *Escherichia coli*: Ion is Dispensable", *J. Bacteriol., vol. 164 (No. 3), pp. 1124-1135 (Dec. 1985).*

(List continued on next page.)

OTHER PUBLICATIONS

C. G. Miller et al., "Degradation of Abnormal Proteins in Peptidase-Deficient Mutants of *Salmonella typhimurium*" *Bacteriol.*, 147 (No. 3), pp. 925–930 (Sep. 1981).

W. F. Prouty et al., "Degradation of Abnormal Proteins in *Escherichia coli*: Formation of Protein Inclusions in Cells Exposed to Amino Acid Analogs", *J. Bio. Chem.*, vol. 250 (No. 3), pp. 1112–1122 (Feb. 1975).

K. R. Rupprecht et al., "Conservation of capR, (lon) DNA of *Escherichia coli* K-12 Between Distantly Related Species", *J. Bacteriol.*, 155 (No. 2), pp. 910–914 (Aug. 1983).

T. J. Silhavy et al., *Experiments with Gene Fusions*, pp. xi–xiii, 119–35, Cold Spring Harbor Laboratory, Cold Spring Harbor, New York (1984).

C. Waghorne et al., "Identification of a Temperature-Sensitive Mutation in the htpR (rpoH) Gene of *Escherichia coli* K-12", *J. Bacteriol.*, 164 (No. 2), pp. 960–963 (Nov. 1985).

J. D. Watson et al., *Recombinant DNA: A Short Course*, Chapter 11, pp. 140–151 (W. H. Freeman and Company 1983).

L. D. Simon et al., "Regulation of the Breakdown of Abnormal Proteins, in *Escherichia Coil*: The T4 Pin Function and other Factors", *Microbiology*—1985, pp. 355–359 (1985).

FIG. 1 INFLUENCE OF htpR MUTATION ON THE LEVEL OF PROTEASE La (Enzyme units)

|  | 30°C | 42°C | % INCREASE |
|---|---|---|---|
| htpR⁻ (K165) | 1.22 | 1.40 | 15 |
| htpR⁺ (SC122) | 2.06 | 3.26 | 58 |

HOSTS AND METHODS FOR PRODUCING RECOMBINANT PRODUCTS IN HIGH YIELDS

The invention described herein was made in the course of work supported by a grant from the National Institutes of Health, U.S. Department of Health and Human Services.

TECHNICAL FIELD OF INVENTION

This invention relates to improved host organisms and methods for producing recombinant products in high yields. More particularly, the present invention relates to cell strains carrying specific mutations within their DNA sequences which cause the organisms to exhibit a reduced capacity for degrading foreign products and the use of these strains as host organisms to produce increased yields of genetically engineered foreign proteins, polypeptides and other products. The methods disclosed in this invention advantageously permit the production, in high yields, of foreign recombinant proteins, polypeptides or other products in hosts which do not usually produce such products.

BACKGROUND ART

The development of recombinant DNA technology has made possible the production of foreign products in host organisms that have been transformed with foreign DNA sequences that code for those products. In general, the DNA coding for the desired amino acid, polypeptide or protein product is introduced into an appropriate site in a cloning vehicle to form a recombinant DNA molecule. That molecule is then used to transform a compatible host and the host cultured to express the inserted DNA sequence and produce the product coded for by that DNA sequence. Such recombinant techniques have been used for the production of eukaryotic and viral proteins in bacterial hosts. These include, for example, leukocyte interferon (S. Nagata et al., "Synthesis In *E. coli* Of A Polypeptide With Human Leukocyte Interferon Activity", *Nature*, 284, pp. 316–20 (1980)), antigens of human hepatitis B virus (C. J. Burrell et al., "Expression In *Escherichia coli* Of Hepatitis B Virus DNA Sequences Cloned In Plasmid pBR322", *Nature*, 279, pp. 43–47 (1979) and M. Pasek et al., "Hepatitis B Virus Genes And Their Expression In *E. coli*", *Nature*, 282, pp. 575–79 (1979)), SV40t antigen (T. M. Roberts et al., "Synthesis Of Simian Virus 40t Antigen In *Escherichia coli*", *Proc. Natl. Acad. Sci. USA*, 76, pp. 5596–600 (1979)), and FMD viral antigens (H. Kupper et al., "Cloning Of cDNA Of Major Antigen Of Foot And Mouth Disease Virus And Expression In *E. coli*", *Nature*, 289, pp. 555–59 (1981)).

The large-scale commercial production of foreign proteins, polypeptides and other products by recombinant DNA techniques has often been limited due to intracellular degradation carried out by the host cell. In a given host organism, foreign or abnormal proteins are rapidly degraded by proteolysis. At high temperatures (above 40° C., for example), normally stable proteins may become susceptible to denaturation, with a resulting increase in abnormal proteins within the cell. In addition, at such high temperatures, the degradation of these abnormal proteins, as well as foreign polypeptides, is more rapid and the cells increase their content of proteolytic enzyme.

The selective degradation of abnormal or foreign proteins requires metabolic energy (J. D. Kowit and A. L. Goldberg, "Intermediate Steps In The Degradation Of A Specific Abnormal Protein In *Escherichia coli*", *J. Biol. Chem.*, 252, pp. 8350–57 (1977) and K. Olden and A. L. Goldberg, "Studies Of The Energy Requirement For Intracellular Protein Degradation In *Escherichia coli*", *Biochim. et Biophys. Acta.*, 542, pp. 385–98 (1978)). An ATP-dependent protease, protease La, catalyzes the initial rate-limiting step in intracellular protein degradation (C. H. Chung and A. L. Goldberg, "The Product Of The lon (capR) Gene In *Escherichia coli* In The ATP-Dependent Protease, Protease La", *Proc. Natl. Acad. Sci. USA*, 78, pp. 4931–35 (1981)); F. S. Larimore et al., "Studies Of The ATP-Dependent Proteolytic Enzyme Protease La In *E. coli*", *J. Biol. Chem.*, 257, pp. 4187–95 (1982) and L. Waxman and A. L. Goldberg, "Protease La From *E. coli* Hydrolyzes ATP And Proteins In A Linked Fashion", *Proc. Natl. Acad. Sci. USA*, 79, pp. 4883–87 (1982)). Protease La is encoded by the lon gene, also referred to as the capR or deg gene (Chung and Goldberg, supra). Mutants in the lon gene contain a defective but partially active protease (Chung and Goldberg, supra; C. H. Chung et al., "Studies Of The Protein Encoded By The lon Mutation capR9 In *Escherichia coli*: A Labile Form Of The ATP-Dependent Protease La That Inhibits The Wild-Type Protease", *J. Biol Chem.*, 258, pp. 215–21 (1983)) and exhibit a reduced capacity to degrade abnormal proteins (S. Gottesman and D. Zipser, "deg Phenotype Of *E. coli* lon Mutants", *J. Bacteriol.*, 133, pp. 844–51 (1978); Kowit and Goldberg, supra). Although lon mutants exhibit a reduced capacity for protein degradation, they still show appreciable degradative activity (approximately ⅓ to ½ normal activity). In addition, their use as hosts in recombinant DNA techniques is limited in terms of viability, due to several undesirable characteristic phenotypes which include greater sensitivity to ultraviolet radiation and overproduction of cell capsular mucopolysaccharides—mucoidy. Mutants which completely eliminate the function of the lon gene have not been available.

The potential of recombinant DNA technology in the commercially feasible production of useful amounts of foreign recombinant products has to date been limited by the absence of viable host organisms characterized by a reduced capacity for degrading foreign products.

DISCLOSURE OF THE INVENTION

The present invention solves the problems referred to above by providing improved host organisms and methods for producing foreign proteins, polypeptides or other products in those host organisms transformed with DNA sequences coding for such products. More particularly, the present invention relates to cell strains carrying specific mutations within their DNA sequences which cause the organisms to exhibit a reduced capacity for degrading foreign products and the use of these strains to produce increased yields of genetically engineered foreign proteins, polypeptides and other products.

By virtue of this invention, it is possible to produce high yields of a desired foreign protein, polypeptide or other product in host organisms which are characterized by a reduced capacity for degrading foreign products.

As will be appreciated from the disclosure to follow, the host organisms and methods of this invention permit the large-scale production of foreign recombinant products in high yields.

BEST MODE OF CARRYING OUT THE INVENTION

In order that the invention herein described may be more fully understood, the following detailed description is set forth.

In the description, the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes, through its template or messenger RNA ("mRNA"), an amino acid, a translation start signal or a translation termination signal. For example, the nucleotide triplets TTA, TTG, CTT, CTC, CTA and CTG encode the amino acid leucine ("Leu"), TAG, TAA and TGA are translation stop signals and ATG is a translation start signal.

Polypeptide—A linear array of amino acids connected one to the other by peptide bonds between the α-amino and carboxy groups of adjacent amino acids.

Gene—A DNA sequence which encodes through its mRNA a sequence of amino acids characteristic of a specific polypeptide.

Transcription—The process of producing mRNA from a gene or DNA sequence.

Translation—The process of producing a polypeptide from mRNA.

Expression—The process of producing a polypeptide from a DNA sequence or gene. It involves transcription and translation.

Plasmid—A nonchromosomal, double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (Tet$^R$) transforms a cell previously sensitive to tetracycline into one which is resistant to it. A host cell transformed by a plasmid or vector is called a "transformant".

Phage or Bacteriophage—Bacterial virus many of which consist of DNA sequences encapsidated in a protein envelope or coat ("capsid").

Cloning Vehicle or Vector—A plasmid, phage DNA or other DNA sequence which is able to replicate in a host cell, characterized by one or a small number of endonuclease recognition or restriction sites at which such DNA sequences may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance.

Cloning—The process of obtaining a population of organisms or DNA sequences derived from one such organism or sequence by asexual reproduction.

Recombinant DNA Molecule or Hybrid DNA—A molecule consisting of segments of DNA from different genomes (the entire DNA of a cell or virus) which have been joined end-to-end outside of living cells and have the capacity to infect some host cell and to be maintained therein.

Expression Control Sequence—A sequence of nucleotides that controls and regulates expression of genes or DNA sequences when operatively linked to those genes or DNA sequences. The term "operatively-linked" includes having an appropriate start signal in front of the gene or DNA sequence encoding the desired product and maintaining the correct reading frame to permit expression of the inserted DNA sequence under the control of the expression control sequence and production of the desired product encoded for by that gene or DNA sequence.

The present invention relates to cell strains carrying specific mutations within their DNA sequences which cause the organism to exhibit a reduced capacity for degrading foreign products and their use as host organisms to produce increased yields of genetically engineering foreign proteins, polypeptides and other products.

The htpR gene of E. coli is a regulatory gene involved in the heat-shock response of the cell. Upon shifts to high temperature, the cell increases the synthesis of a number of polypeptides referred to as "heat-shock proteins" (F. C. Neidhardt et al., "Molecular Cloning And Expression Of A Gene That Controls The High-Temperature Regulon Of *Escherichia coli*", *J. Bacteriol.*, 153, pp 597–603 (1983); T. Yamamori et al, "*Escherichia coli* Gene (hin) Control Of Transcription Of Heat Shock Operons And Cell Growth At High Temperatures"; F. C. Neidhardt, "The High Temperature Regulon Of *Escherichia coli*", in *Heat Shock From Bacteria To Man*, M. J. Ashburner et al. (eds.), Cold Spring Harbor Laboratory, pp. 131–38; 139–45 (1982)). We have discovered that one of these heat-shock proteins is protease La, an ATP-dependent protease which carries out the rate-limiting step in the selective degradation of abnormal proteins within the cell. The heatshock response does not occur in htpR mutants, also referred to as hin mutants. Furthermore, these mutants exhibit a reduced capacity to synthesize the heat-shock proteins at low temperatures, for example, 30° C. (Ashburner et al., supra). Such mutants can be obtained by those skilled in the art using standard mutagenesis techniques.

Figure 1:
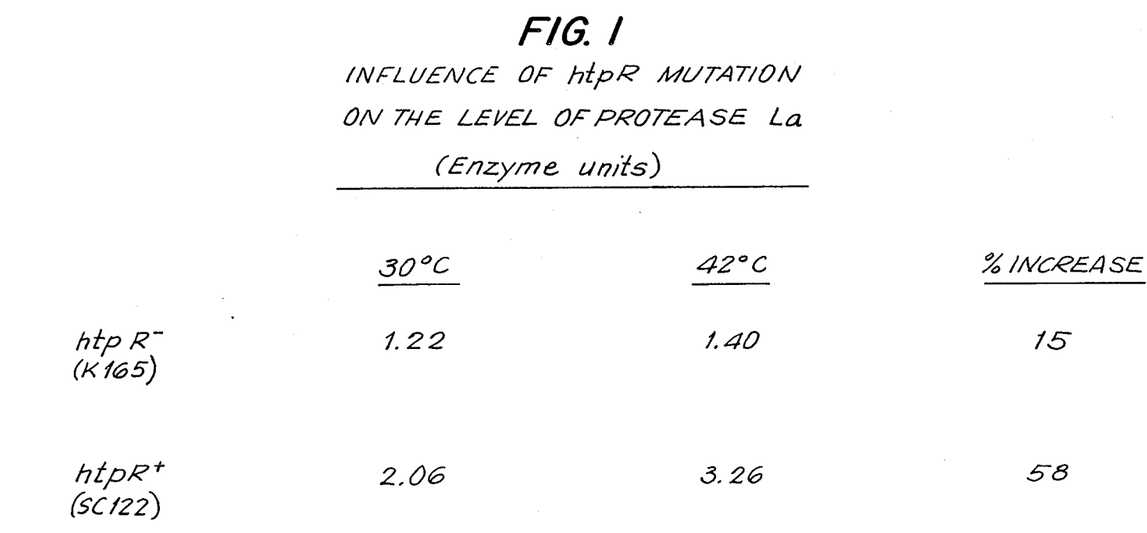
FIG. 1 is a table which indicates the level of protease La isolated from htpR mutants at 30° and 42° C.

Our studies of the effect of htpR mutation on the cellular protein degradation process indicate that the htpR gene controls the transcription of the lon gene encoding protease La. In htpR mutants, there is reduced transcription of the lon gene, resulting in the reduced production of protease La which, in turn, leads to a decrease in the capacity of the mutant to degrade abnormal proteins. This reduced capacity to degrade aberrant proteins is evident under both high and low temperature conditions (e.g., 42° C. and 30° C., respectively). Furthermore, the level of protease La isolated from these cells is lower at 30° C. in the mutant and does not increase on transfer to 42° C. (FIG. 1). The table in FIG. 1 illustrates the level of protease La isolated from htpR mutants at 30° and 42° C. Data set forth in the table was obtained using *E. coli* cultures grown at 30° and shifted to 42° C. for 1 hour. Protease La activity was measured with the specific fluorometric substrate glutaryl-alanyl-phenylalanyl-methoxynaphthylamine after partial purification of the enzyme by phosphocellulose chromatography, as described by L. Waxman and A. L. Goldberg in *J. Biol. Chem.* (1984) [in press]. The htpR mutations therefore appear to affect the basal level of protease La and prevent its increased production upon temperature shift.

The reduced degradative capacity exhibited by htpR mutants is greater than or equal to that found in lon mutants which encode a defective protease La. However, the htpR mutants do not demonstrate the undesirable phenotypes exhibited by lon mutants, such as the overproduction and accumulation of capsular polysaccharides (also referred to as mucoidy), defective cell division and filament formation and increased sensitivity to ultraviolet radiation or other DNA-damaging agents. The htpR mutants are therefore more viable than lon mutants. This viability provides a distinct advantage in the utilization of htpR mutants as host organisms in recombinant DNA techniques to increase the yields of expressed foreign proteins and other products.

Utilizing P1-mediated transduction, we have constructed htpR lon mutants which contain both an htpR mutation and a mutation within the lon gene, for example, lonΔ100 or capR9. These double mutants produce a labile protease in reduced amounts and exhibit less capability to degrade abnormal proteins than strains carrying either mutation alone. The defect in proteolysis by these double mutants is greater than that found in any known strain. These double mutants are viable hosts which achieve high cell densities in culture. Like the htpR mutants, they do not suffer from mucoidy or the other unhealthy characteristics exhibited by lon mutants.

Thus, the htpR lon mutants of this invention are particularly useful for the large-scale production of genetically engineered proteins which are usually subject to rapid intracellular degradation. According to this invention, a foreign product may be produced using lon mutants, htpR mutants or htpR lon mutants by a method comprising the steps of inserting a DNA sequence coding for the product or a portion thereof into a cloning vehicle so that there is functional attachment therein to an expression control sequence; transforming a host with said cloning vehicle that has the inserted DNA sequence therein, said host characterized by a reduced capacity for degrading foreign products; culturing said transformed host; and collecting the product from said culture. Foreign products may also be produced from such organisms by culturing a host transformed with a recombinant DNA molecule characterized by a DNA sequence coding for the product, said host characterized by a reduced capacity for degrading foreign products; and collecting the product from said culture.

The mutant strains of this invention may be advantageously utilized as host cells into which recombinant DNA sequences are introduced by any technique known in the art and expressed in the form of proteins, polypeptides and other products. The decreased capacity of these mutant strains to degrade foreign or aberrant polypeptides permits the production of recombinant proteins and other products in high yields. When the mutant strains of this invention are used in combination with expression control sequences, the expression of a desired foreign protein or product is further enhanced.

Typically, the level of synthesis of a polypeptide in a host cell is governed by three major factors: the number of copies of the DNA sequence that codes for the product within the cell, the efficiency with which those DNA sequences are transcribed and the efficiency with which the resultant messenger RNA ("mRNA") is translated. Efficiency of transcription and translation (which together comprise expression) is in turn dependent upon the nucleotide sequences which are normally situated ahead of the sequences coding for the desired products. These nucleotide sequences or expression control sequences define, inter alia, the location at which RNA polymerase interacts (the promoter sequence) to initiate transcription and at which ribosomes bind and interact with the mRNA (the product of transcription) to initiate translation of the desired product.

A variety of expression control sequences are available to improve the efficiency of expression (transcription and translation) of cloned DNA sequences. These expression control sequences are of two main types—constitutive expression control sequences and controllable expression control sequences. Constitutive expression control sequences, such as β-lac, continuously function during host cell growth to express the cloned DNA sequence and to produce the product coded for by that DNA sequence. Controllable expression control sequences, such as trp, $\lambda P_L$, or $\lambda P_R$ may be regulated, i.e., switched on or off, during host cell growth so that expression of the cloned DNA sequence may be "switched on" at the most appropriate time in a culture's growth cycle. For example, controllable expression control sequences may be switched off to enable the host cells to propagate without excessive build-up of gene products and then switched on to promote the expression of large amounts of the desired protein products which are under the control of those expression control sequences. Because over-production of even normally non-toxic gene products may be harmful to host cells and lead to decreased stability of particular host-vector systems, a controllable expression control sequence is often favored so as to modulate expression during host cell growth.

Several controllable expression control sequences can be employed to express DNA sequences and genes coding for proteins and polypeptides in host organisms. These include, for example, the operator, promoter and ribosome binding and interaction sequences of the lactose operon of *E. coli* (e.g., K. Itakura et al., "Expression In *Escherichia coli* Of A Chemically Synthesized Gene For The Hormone Somatostatin", *Science*, 198, pp. 1056–63 (1977); D. V. Goeddel et al., "Expression In *Escherichia coli* Of Chemically Synthesized Genes For Human Insulin", *Proc. Natl. Acad. Sci. USA*. 76, pp. 106–10 (1979)), the corresponding sequences of the tryptophan synthetase system of *E. coli* (J. S. Emtage et al., "Influenza Antigenic Determinants Are Expressed From Haemagglutinin Genes Cloned In *Escherichia coli*", *Nature*, 283, pp. 171–74 (1980); J. A. Martial et al., "Human Growth Hormone: Complementary DNA Cloning And Expression In Bacteria", *Science,* 205, pp. 602–06 (1979)) and the major operator and promoter regions of phage λ (H. Bernard et al., "Construction Of Plasmid Cloning Vehicles That Promote Gene Expression From The Bacteriophage Lambda $P_L$ Promoter", *Gene,* 5, pp. 59–76 (1979)).

The fact that the htpR and htpR lon mutants of the present invention exhibit a reduced capacity to degrade foreign proteins at high temperatures makes them particularly suited for use in combination with temperature-inducible controllable expression control sequences. A heat-inducible expression sequence, the $P_L$ promoter of bacteriophage lambda for example, can be fused to a DNA sequence encoding a desired protein by standard techniques known in the art. The resultant recombinant DNA sequence can then be used to transform an htpR or htpR lon mutant host organism. When grown at 42° C., such hosts express the desired protein or product to an enhanced degree, due to the temperature-induced expression control sequence switched on at that temperature. In addition, the expression of the desired protein or product is further enhanced due to the reduced capacity of these hosts to degrade foreign proteins and products. Further improvement of the yield of expressed proteins may be obtained by inserting the recombinant DNA molecule containing the expression control sequence into a higher copy number plasmid or a bacteriophage derivative in order to increase the number of gene copies within the cell. Thus, use of the htpR and htpR lon mutants of this invention in combination with heat-inducible expression control sequences allows increased expression of genetically engineered proteins, polypeptides and other products. It is to be understood, however, that since the htpR and htpR lon mutants exhibit reduced degradation of foreign proteins at low temperatures (e.g., 30° C.), the present invention also permits the enhanced expression of foreign proteins or other products utilizing non-temperature inducible as well as constitutive expression control sequences.

It should also be noted that, although the present invention has been herein described as utilizing htpR and htpR lon mutants as host cells in recombinant DNA techniques, the htpR mutation itself may be inserted into host cells in which the corresponding gene has been eliminated. These host cells can then be transformed with recombinant DNA sequences, i.e., encoding the desired proteins, and will produce those proteins in high yields.

The host organisms and methods of this invention are applicable to the production of a wide variety of proteins and polypeptides. In addition, the methods of this invention may be employed to enhance the production of other products whose yields depend upon high levels of enzymes that are otherwise subject to degradation. For example, products such as the active components of vaccines or other pharmaceutically active products, agriculturally or other commercially useful compositions, enzymes, hormones, amino acids, industrial chemicals, antibiotics, foodstuffs, and the like can be usefully produced by the methods of this invention. Other products that may be produced by the methods of this invention include polypeptides displaying an immunological or biological activity of leukocyte interferon, fibroblast interferon or other interferons, polypeptides having the antigenicity of FMDV viral antigens or hepatitis B viral antigens, polypeptides displaying the biological activity of human or animal hormones such as proinsulin and polypeptides and proteins displaying an immunological or biological activity of human, animal or viral products. The selection of a particular product is not part of this invention. Rather, the invention is applicable generally to the increased expression of DNA sequences coding for such products and to the production of such products in the mutant host organisms of the invention.

It should be understood that the present invention also includes host organisms containing any of a number of possible mutations within the htpR or lon genes, or combinations thereof. Such mutants may be obtained utilizing standard mutagenesis and selection techniques. Furthermore, the methods of this invention are applicable to the production of foreign proteins and products in strains of *E. coli* carrying a specific mutation within its DNA sequence which causes the organism to exhibit a reduced capacity for degrading foreign products.

The methods of this invention are also applicable to the production of foreign proteins and products in other prokaryotic and eukaryotic hosts including *E. coli,* bacilli, yeasts, fungi, animal or plant cells or other host organisms. The heat-shock response appears to be a universal mechanism for the protection of the cell from the adverse condition of high temperature (Ashburner et al., supra). We have observed ATP-dependent proteases analogous to protease La in other bacteria, such as *Salmonella typhimeurium* and *Bacillus subtilis.* Lon mutants have been detected in *Salmonella typhimeurium.* It is therefore likely that a mechanism for abnormal or foreign protein degradation similar to that found in *E. coli* is to be found in all prokaryotes. This mechanism may also exist in eukaryotic organisms. An enzyme similar to protease La has been found in the mitochondria of mammalian cells. The existence of such mechanisms in these other organisms permits the use of the methods of this invention to construct mutant host organisms defective in the gene which functionally corresponds to the protease La gene present in *E. coli* and which, like the mutant organisms described herein, exhibit a reduced capacity to degrade foreign products.

In order that this invention may be better understood, the following examples are set forth. These examples are for purposes of illustration only and are not to be construed as limiting the scope of the invention in any manner.

EXAMPLE 1

The following example is illustrative of the methods for constructing the htpR lon mutants of the present invention.

Construction Of htpR lon Mutants

*E. coli* cells (strain SG900, non-suppressor, lon+, tsx+, htpR+) were infected with λNK55, a bacteriophage defective in DNA synthesis in non-suppressor hosts and which carries the Tn10 transposon in its CIII gene. The Tn10 transposon, a 9300 base pair transposable piece of DNA with inverted terminal repeat sequences, inserts itself into the tsx gene on the *E. coli* chromosome at approximately 10 min on the genetic map. The resulting region of the chromosome is designated tsx: Tn10.

Since Tn10 carries a gene for tetracycline resistance and since the transposon inserts itself into the tsx gene which codes for the bacteriophage T6 receptor, *E. coli* cells carrying the Tn10 insert will be tetracycline resistant and resistant to T6 infection. The λND55 infected cells were, therefore, selected for resistance to tetracycline and these colonies further selected for resistance to T6 phage. Since the lon gene of *E. coli* is located near the tsx gene, the resulting isolates contained the lon gene linked to the tetracycline resistance marker of tsx: Tn10.

The linked lon and tsx: Tn10 genes were next introduced into a lon⁻ *E. coli* strain, such as lonΔ100, by P1-mediated transduction. Cells containing crossovers between the lon gene of the mutant strain and the tsx: Tn10 gene of the P1 transducing element were selected for resistance to tetracycline and screened for the mucoid phenotype typical of lon mutants. The resulting isolates were lon mutants linked to the tetracycline resistance marker of Tn10 (lon⁻, tet$^r$).

To construct double mutant strains containing mutations in the lon gene and the htpR gene, which controls the heat shock response, the lon⁻: tet$^r$ sequence of the above-described isolates was introduced into an htpR mutant *E. coli* strain, such as *E. coli* strain K165 or GW4701, lon⁺, htpR⁻, by P1-mediated transduction. The double mutants were selected for tetracycline resistance and then screened for temperature sensitivity. It is to be understood that, although the double mutant described herein was constructed by introduction of the lon⁻ gene into an htpR⁻ strain, the reverse sequential construction, i.e., introduction of the htpR⁻ gene into a lon⁻ strain, may also be employed.

The resulting isolates, htpR⁻ lon⁻ double mutants, such as *E. coli* strain SG935 and SG927, lonΔ100, htpR⁻, may be used according to the present invention to increase the yields of genetically engineered foreign proteins produced in *E. coli*. Similarly, *E. coli* strains SG936 and SG928, lonR9, htpR⁻, may be produced and used according to the processes disclosed herein.

EXAMPLE 2

Measurement Of Protein Degradation In htpR Mutants

The following example is illustrative of the methods for measuring protein degradation in the mutant strains of this invention.

A culture of the mutant strain to be examined was grown up overnight, preferably in minimal M9 media (J. H. Miller, *Experiments In Molecular Genetics* (Cold Spring Harbor Laboratory, 1981)). In the morning, 10 ml cultures were set up in Klett flasks and preferably the cells were allowed to grow at least two generations to verify that they were growing well.

When the cells were in early log phase, 0.2 ml–0.5 ml of 5 mg/ml H₂O puromycin (filter sterilized) was added to each flask. The density of the cell cultures was such that at the end of the next 20 minute period, the cells would be in mid log phase. The final concentration of puromycin in each flask was 100–250 μg/ml. Puromycin is an inhibitor of protein synthesis which was incorporated into the growing polypeptides of the cells. This incorporation, after some time, resulted in the formation of abnormal prematurely terminated proteins. Such short proteins, like many cloned proteins of commercial interest, such as proinsulin, are ordinarily rapidly degraded by bacteria (A. L. Goldberg, *Proc. Natl. Acad. Sci. USA*, 69, pp. 2640–44 (1972)).

After addition of the puromycin, the cells were incubated for 15 min at 37° C. One μCi of ³H-amino acid/ml was then added to the cultures to label the proteins being synthesized by the cells. (If the cells are grown in rich LB media, ³²S-methionine is the preferred label and 4 μCi³⁵S-methionine/ml should be used.) The cultures were incubated with the radioactive label for 5 min at 37° C. The cells were immediately centrifuged in sterile 40 ml centrifuge tubes using a Sorvall SS-34 rotor for 1 min at 5000 rpm. The supernatant was rapidly decanted and the pellets washed by resuspension and vortexing in 2 volumes of media containing 1 mg/ml cold chaser amino acid. The cells were respun as before, resuspended in the cold chaser amino acid-containing media and transferred to Klett flasks. When transferred to these flasks, the cell density was adjusted such that at the end of the following 60 or 90 minute time course, the cells were not in stationary phase.

At this point in the procedure, the puromycin treated cells contained growing polypeptides with puromycin and labelled amino acids incorporated within their sequences. The puromycin caused these polypeptides to become disassociated from the ribosomes on which they were being synthesized and the resulting abnormal polypeptides were degraded by the bacterial cell.

To measure the rate at which a particular cell strain degraded these prematurely terminated proteins, samples were taken from the supernatant of the culture at different times and measured for free radioactive amino acids which resulted from the degradative process.

At t=0, two 0.5 ml samples were taken from each culture. One was designated as "total counts" and represented total radioactive protein at t=0. This sample was transferred to a tube maintained on ice and containing 100 μl of 70% TCA (trichloracetic acid). To this sample was added 0.1 ml of H₂O. The second sample taken at t=0 was designated "blank" and represented the acid soluble counts, i.e., free radioactive amino acids, present in the sample at t=0. This 0.5 ml sample was also transferred to a tube on ice containing 100 μl of 70% TCA. The final TCA concentration was, preferably, 10%. To this sample was added 100 μl of 10% BSA (bovine serum albumin). At t=15, 30, 60, and 90 minutes, similar 0.5 ml samples were taken from the cell culture and added to 10% TCA with 100 μl 10% BSA.

Each sample was incubated on ice in the TCA solution for 30 min. Free radioactive amino acids in each sample were solubilized in the TCA, while nondegraded proteins remained insoluble and precipitated out of the TCA. Thus, protein degradation was determined by measuring the conversion of labelled proteins which were insoluble in TCA into free radioactive amino acids soluble in TCA. The production of TCA soluble counts over time was therefore utilized as an indication of the rate of protein degradation within the cells. It should be noted that the rate of degradation of the puromycyl proteins is very high and required performance of the above-described TCA precipitation steps as quickly as possible.

After incubation in TCA solution, all samples (except those for "total counts") were spun at 4° C. in the IEC centrifuge, rotor #269, for 10 min at 3500 rpm and 0.4 ml of the supernatant of each sample was counted in 4 ml Liquiscint scintillation fluid for 5 min. The counts in each sample were used to calculate the % protein degradation based on the formula:

% protein degradation =

$$\frac{\text{Average } cpm \text{ (time point)} - \text{Blank } cpm(t = 0)}{\text{Total counts } cpm} \times 100$$

Figure 2:
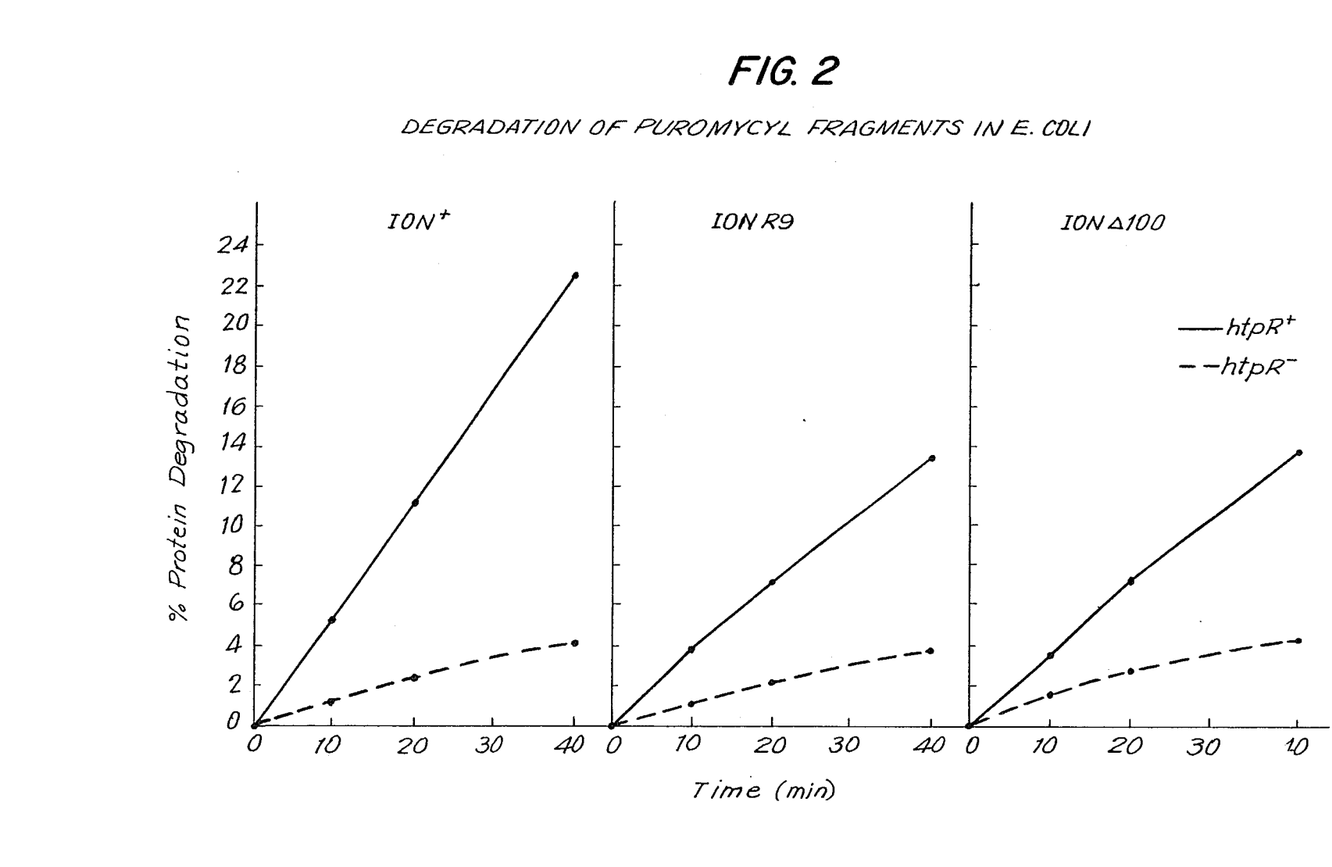
FIG. 2 is a comparative graphical presentation of the percentage of degradation vs. time for various incomplete E. coli polypeptides that have incorporated puromycin.

FIG. 2 indicates the percentage of puromycyl protein degradation over time in a wild type *E. coli* cell (lon⁺, htpR+) versus an htpR mutant (lon+, htpR−) (see graph 1, using strain SC122 (htpR+) and K165 (htpR−), gifts from Dr. Graham Walker) and the degradation in various lon mutants and htpR lon double mutants (see graphs 2 and 3). As is apparent from the figure, the htpR mutation significantly decreased the percentage of protein breakdown within the cell in both wild type and lon mutant cells.

While the above-described example involved degradation of short polypeptides resulting from the incorporation of puromycin, similar effects of the htpR mutation were also demonstrated by following the rapid degradation of full length abnormal proteins containing amino acid analogs such as canavanine. The procedure is similar to that described above. At mid-log phase, cells grown overnight in M9 media were centrifuged and resuspended in arginine-free media. Canavanine, an amino acid analog of arginine, was added to a 0.6 mM final concentration. After 15 min, 10–20 $\mu$Ci $^3$H-phenylalanine was added. After 5 min, the culture was centrifuged and resuspended in media containing 0.6 mM arginine and cold phenylalanine at 0.5–1.0 mg/ml. The cultures were then respun and resuspended in the same media.

Figure 3:
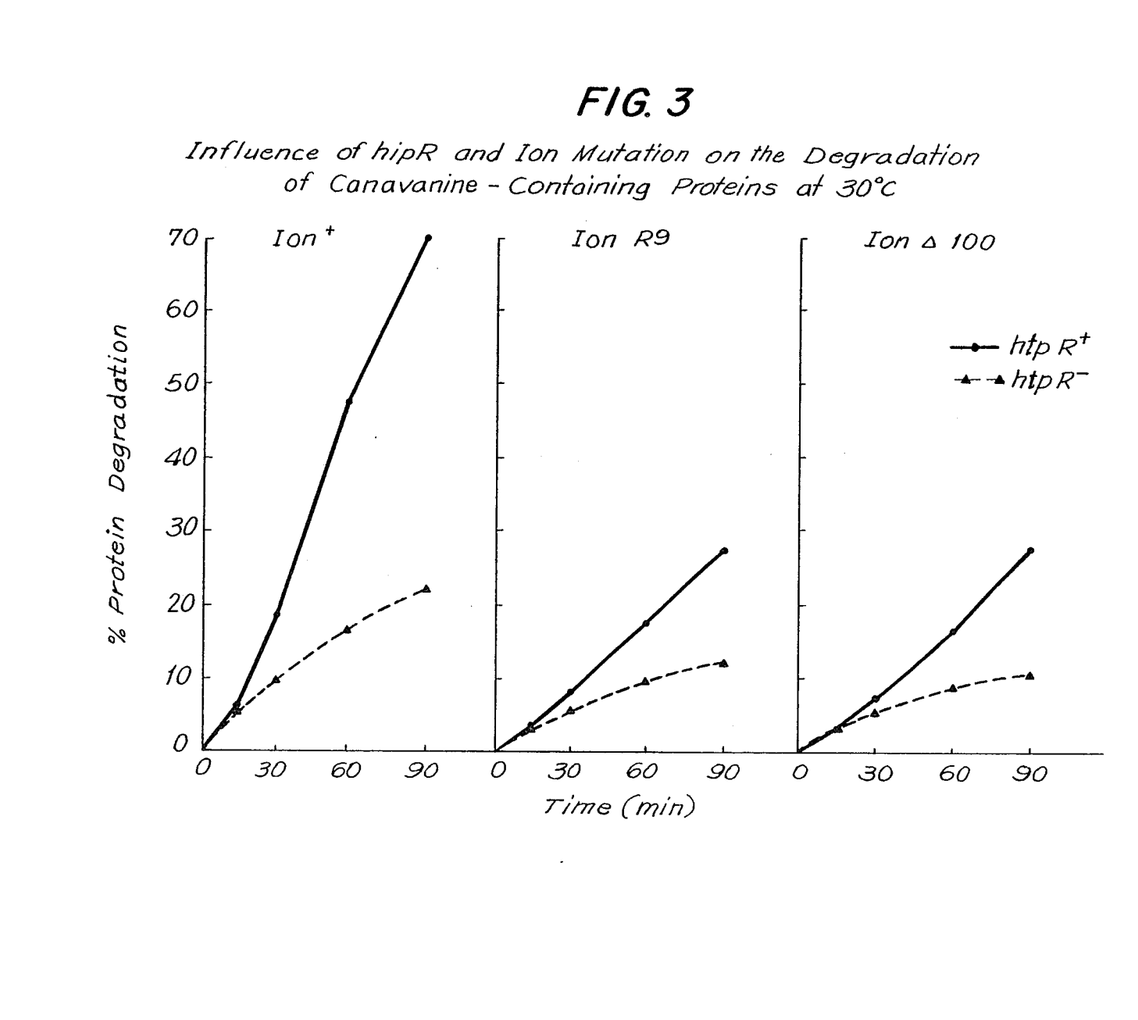
FIG. 3 is a comparative graphical presentation of the percentage of degradation vs. time for various abnormal E. coli proteins that contain canavanine in place of arginine.

Samples were taken from the cultures in the identical manner as described above for the puromycin determination and the percentage of canavanine-containing proteins determined using the same formula. FIG. 3 indicates the percentage of protein degradation over time of a wild type E. coli cell (lon+, htpR+) versus an htpR mutant (lon+, htpR−) (see graph 1, using strain GW1000 (htpR+) and GW4701. (htpR−), gifts from Dr. Graham Walker) and the protein degradation in various mutants and htpR lon double mutants (see graphs 2 and 3). The htpR mutation clearly decreased the protein breakdown in both the wild type and lon mutant cells. Furthermore, the double mutants, i.e., those carrying both htpR and lon mutations, showed a greater decrease in degradation than cells carrying only the htpR mutation alone, indicating that the double mutation provides some additive effect on protein degradation.

Microorganisms prepared by the processes described herein are exemplified by cultures deposited in the American Type Culture Collection, Rockville, Maryland. Cultures deposited on Mar. 5, 1984 are there identified as follows:
Culture SG935: ATCC 39623
Culture SG936: ATCC 39624
Cultures deposited on Mar. 6, 1984 are there identified as follows:
Culture SG927: ATCC 39627
Culture SG928: ATCC 39628

While we have hereinbefore presented a number of embodiments of this invention, it is apparent that our basic construction may be altered to provide other embodiments which utilize the processes and compositions of this invention. Therefore, it will be appreciated that the scope of this invention is to be governed by the claims appended hereto rather than the specific embodiments which have been presented hereinbefore by way of example.

We claim:

1. A method for producing a polypeptide in a bacterial host organism comprising the steps of:
   (a) inserting a non-htpR DNA sequence coding for a polypeptide into a cloning vehicle so that said DNA sequence is under the regulation of a functional expression control sequence;
   (b) transforming a bacterial host with said cloning vehicle that has the inserted DNA sequence therein, said host carrying a mutation in a heat-shock regulatory gene that results in a reduced proteolytic degrading capacity for said polypeptide; and
   (c) culturing said transformed host.

2. A method for producing a polypeptide in a bacterial host organism comprising the step of culturing a bacterial host transformed with a recombinant DNA molecule characterized by a non-htpR DNA sequence coding for said polypeptide, said host carrying a mutation in a heat-shock regulatory gene that results in a reduced proteolytic degrading capacity for said polypeptide.

3. The method of claim 1 or 2 wherein the bacterial host organism is selected from the group consisting of htpR mutants and htpR lon mutants.

4. The method of claim 3 wherein the htpR lon mutant host organism is selected from the group consisting of E. coli strain SG927, E. coli strain SG928, E. coli strain SG935, and E. coli strain SG936.

5. The method of claim 1 or 2 wherein said non-htpR DNA sequence is selected from the group consisting of DNA sequences that code for polypeptides displaying an immunological or biological activity of leukocyte interferon, DNA sequences that code for polypeptides displaying an immunological or biological activity of fibroblast interferon, DNA sequences that code for other interferons, DNA sequences that code for polypeptides having the antigenicity of FMDV viral antigens, DNA sequences that code for polypeptides having the antigenicity of hepatitis B viral antigens, DNA sequences that code for polypeptides displaying the biological activity of proinsulin and other human or animal hormones, and DNA sequences that code for other polypeptides and proteins displaying an immunological or biological activity of human, animal or viral products.

6. The method of claim 1 or 2 wherein the expression control sequence is heat-inducible.

7. The method of claim 1 or 2 wherein the bacterial host organism is selected from the group consisting of strains of E. coli, Bacillus subtilis, and Salmonella typhimurium.

* * * * *